(12) United States Patent
Hertzoff et al.

(10) Patent No.: US 10,561,860 B2
(45) Date of Patent: Feb. 18, 2020

(54) IMAGING BEAM POSITIONING APPARATUS AND METHOD OF USE THEREOF

(71) Applicants: Jennifer Hertzoff, Tempe, AZ (US); Hermann A. Hofer, Phoenix, AZ (US)

(72) Inventors: Jennifer Hertzoff, Tempe, AZ (US); Hermann A. Hofer, Phoenix, AZ (US)

( * ) Notice: Subject to any disclaimer, the term of this patent is extended or adjusted under 35 U.S.C. 154(b) by 437 days.

(21) Appl. No.: 15/360,771

(22) Filed: Nov. 23, 2016

(65) Prior Publication Data

US 2018/0140262 A1 May 24, 2018

(51) Int. Cl.
*A61N 5/10* (2006.01)
*A61B 6/08* (2006.01)
(Continued)

(52) U.S. Cl.
CPC .............. *A61N 5/1049* (2013.01); *A61B 5/70* (2013.01); *A61B 6/08* (2013.01); *A61B 6/14* (2013.01);
(Continued)

(58) Field of Classification Search
CPC ........... A61B 5/70; A61B 6/04; A61B 6/0492; A61B 6/08; A61B 6/58; A61B 6/589; A61B 90/30; A61B 90/35; A61B 90/36; A61B 90/39; A61B 2090/3937; A61B 2090/3945; A61B 2090/397; A61B 2090/3975; A61B 2090/3979; H05G 1/02; G01C 15/002; G01C 15/004; G01B 7/001; G01B 7/003; G01B 7/02; G01B 9/08; G01B 11/02; G01B 11/028; G01B 21/16; A61N 5/1048; A61N 5/1049; A61N 5/105; A61N 5/1056; A61N 5/1069; G21K 1/02; G21K 1/04; G21K 5/04; G21K 5/10; G21K 2201/00; G01N 2201/022; G01N 2201/0221; G01N 2201/0227; G01N 2201/024; G01N 2201/0245; G01N 2201/025;
(Continued)

(56) References Cited

U.S. PATENT DOCUMENTS 5,553,115 A * 9/1996 Odaka ...................... A61B 6/08
378/170
5,745,545 A * 4/1998 Hughes ..................... A61B 6/08
378/206
(Continued)

*Primary Examiner* — Anastasia Midkiff
(74) *Attorney, Agent, or Firm* — Skinner and Associates; Joel Skinner

(57) ABSTRACT

The invention comprises an alignment guide apparatus and a method of use thereof for aligning an imaging beam, longitudinally passing through an exit nozzle of an imaging system, to an imaging zone of a sample, includes the steps of: (1) providing an alignment guide, the alignment guide comprising: (a) a guide wall at least partially circumferentially enclosing an aperture, (b) a first laser element connected to the guide wall, and (c) a second laser element connected to the guide wall; (2) inserting the exit nozzle of the imaging system into the aperture; (3) projecting a first line from the first laser element onto the sample; (4) projecting a second line from the second laser element onto the sample; and (5) moving the sample relative to the exit nozzle of the imaging system to position an intersection of the first line and the second line at the imaging zone to align the imaging beam to the imaging zone.

13 Claims, 3 Drawing Sheets

(51) Int. Cl.
*A61B 6/14* (2006.01)
*A61B 6/00* (2006.01)
*G21K 5/04* (2006.01)
*A61B 90/35* (2016.01)
*A61B 5/00* (2006.01)
*H01J 37/22* (2006.01)
*H01J 35/16* (2006.01)
*G01C 15/00* (2006.01)
*A61B 90/30* (2016.01)
*A61B 90/00* (2016.01)

(52) U.S. Cl.
CPC .............. *A61B 6/587* (2013.01); *A61B 6/589* (2013.01); *A61B 90/35* (2016.02); *G21K 5/04* (2013.01); *H01J 35/165* (2013.01); *H01J 37/226* (2013.01); *A61B 90/30* (2016.02); *A61B 2090/3945* (2016.02); *A61N 2005/1056* (2013.01); *G01C 15/004* (2013.01); *G01N 2201/0245* (2013.01); *G01N 2201/06106* (2013.01); *H01J 2237/045* (2013.01); *H01J 2237/0456* (2013.01); *H01J 2237/1501* (2013.01); *H01J 2237/2482* (2013.01)

(58) Field of Classification Search
CPC ....... G01N 2201/0253; G01N 2201/06; G01N 2201/061; G01N 2201/06106; G01N 2201/06113; G01N 2201/0612; G01N 2201/062; G01N 2201/0626; G01N 2201/063; G01N 2201/0633; G01N 2201/066; G01N 2201/0662; G01N 2201/08; G01N 2201/082; H01J 5/02; H01J 5/16; H01J 5/18; H01J 35/02; H01J 35/14; H01J 35/16; H01J 35/165; H01J 35/32; H01J 37/02; H01J 37/16; H01J 37/165; H01J 37/21; H01J 37/22; H01J 37/226; H01J 37/3005; H01J 37/3045; H01J 2235/16; H01J 2235/163–166; H01J 2237/02; H01J 2237/026; H01J 2237/04; H01J 2237/045; H01J 2237/0451; H01J 2237/0456; H01J 2237/15; H01J 2237/1501; H01J 2237/16; H01J 2237/20; H01J 2237/20292; H01J 2237/248; H01J 2237/2482

See application file for complete search history.

(56) References Cited

U.S. PATENT DOCUMENTS

| | | | |
|---|---|---|---|
| 7,147,371 B2 * | 12/2006 | Hecker | A61B 6/08 378/206 |
| 7,380,986 B2 * | 6/2008 | Brandstatter | A61B 6/08 378/206 |
| 9,439,619 B1 * | 9/2016 | Nance | A61B 6/587 |
| 2004/0141590 A1 * | 7/2004 | Ihalainen | A61B 6/08 378/206 |
| 2012/0163539 A1 * | 6/2012 | van der Veen | H01J 35/32 378/65 |

* cited by examiner

IMAGING BEAM POSITIONING APPARATUS AND METHOD OF USE THEREOF

BACKGROUND OF THE INVENTION

Field of the Invention

The invention relates generally to guiding a process of imaging a sample.

Discussion of the Prior Art

Imaging System

Use of an imaging system with an imaging beam requires alignment of the imaging beam and a sample. Alignment of the imaging beam to the sample or vise-versa is often complicated by the imaging beam comprising: (1) wavelengths and/or photons out of the visible portion of the electromagnetic spectrum and/or (2) particles not visible to the human eye.

SUMMARY OF THE INVENTION

The invention comprises an alignment apparatus and method of use thereof for aligning an imaging beam of an imaging apparatus to a sample.

DESCRIPTION OF THE FIGURES

A more complete understanding of the present invention is derived by referring to the detailed description and claims when considered in connection with the Figures, wherein like reference numbers refer to similar items throughout the Figures.

Figure 1:
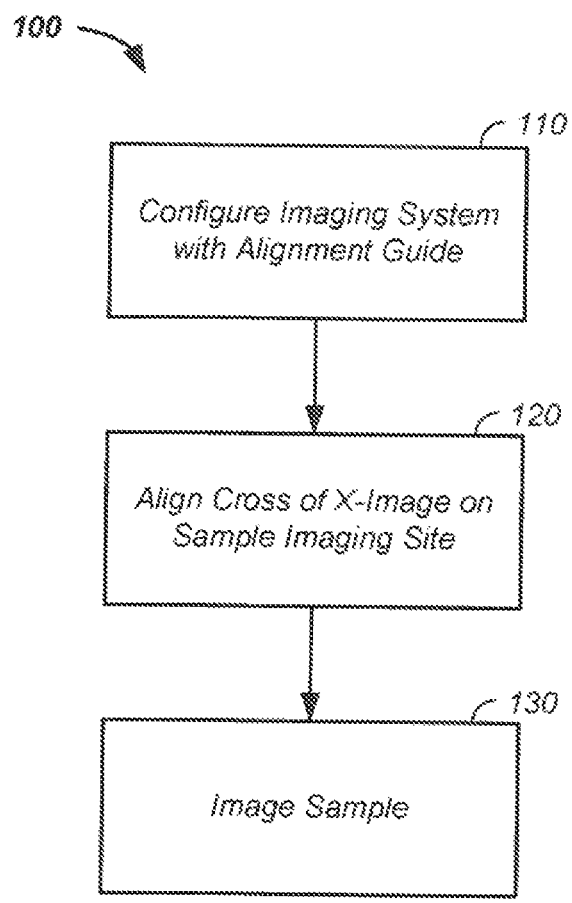
FIG. 1 illustrates use of an image alignment system.

Elements and steps in the figures are illustrated for simplicity and clarity and have not necessarily been rendered according to any particular sequence. For example, steps that are performed concurrently or in different order are illustrated in the figures to help improve understanding of embodiments of the present invention.

Problem

There exists in the art of imaging a need for accurate, precise, and rapid alignment of the sample relative to an imaging beam or two-dimensional imaging beam.

DETAILED DESCRIPTION OF THE INVENTION

The invention comprises an image alignment guide configured to attach to an output nozzle of an imaging system.

For example, an alignment guide and a method of use thereof for aligning an imaging beam, longitudinally passing through an exit nozzle of an imaging system, to an imaging zone of a sample, includes the steps of: (1) providing an alignment guide, the alignment guide comprising: (a) a guide wall at least partially circumferentially enclosing an aperture, (b) a first laser element connected to the guide wall, and (c) a second laser element connected to the guide wall; (2) inserting the exit nozzle of the imaging system into the aperture; (3) projecting a first line from the first laser element onto the sample; (4) projecting a second line from the second laser element onto the sample; and (5) moving the sample relative to the exit nozzle of the imaging system to position an intersection of the first line and the second line at the imaging zone to align the imaging beam to the imaging zone.

In one example, the alignment guide attaches to an X-ray tube head of an X-ray generator and/or dental X-ray unit, such as at the terminal end of the X-ray tube head. For clarity of presentation and without loss of generality, herein a nozzle refers to the output tube of an X-ray system, such as but not limited to: (1) a handheld X-ray system or (2) a fixed location, dynamically adjustable X-ray system. A non-limiting example of the handheld X-ray system is the Nomad™ (Aribex, Orem, Utah) series of handheld dental X-ray systems. The nozzle optionally is an output unit of the X-ray system that: (1) contains an X-ray generation system or (2) does not contain an X-ray generation system, but is linked to the X-ray generation system.

For clarity of presentation and without loss of generality, herein the sample, object, and/or target of the alignment guide and/or the X-ray unit is a tooth, root of a tooth, and/or portion of a pet.

Herein, a z-axis is aligned with the imaging beam and hence moves as the imaging beam is moved. The x- and y-axes form a plane perpendicular to the x-axis, such as tangential to an outer surface of the sample at an input point of the z-axis into the sample.

Herein, for clarity of presentation and without loss of generality, an X-ray beam is used to represent the imaging beam and a house pet is used to represent the sample. However, generally, the imaging beam of the imaging system uses X-rays, such as from 0.01 to 10 nanometers; ultraviolet light, such as from 200 to 400 nm; or infrared light, such as from 700 to 10,000 nm. Herein, the imaging beam is a narrow beam, such as along a line or an expanding beam, such as intersecting a two-dimensional detector array. The house pet is representative of any animal, person, body part, object, or sample to be imaged.

Herein, a laser is of any type and/or emits light at any wavelength.

Herein, an imaging zone is a preferred point, region, or area of intersection of the imaging beam with an incident surface of the sample to yield an image of a desired volume of the sample.

Image Alignment System Referring now to FIG. 1, an image alignment system 100 is illustrated. The image alignment system 100 includes: a first task 110 of installing an alignment guide 200, also referred to as an imaging alignment guide, on the imaging system; a second task 120 of aligning a visible output of the alignment guide, such as an X-image on a desired imaging site of the sample 310; and a third task 130 of acquiring an image of the sample. The alignment guide 200 is further described, herein.

Figure 2:
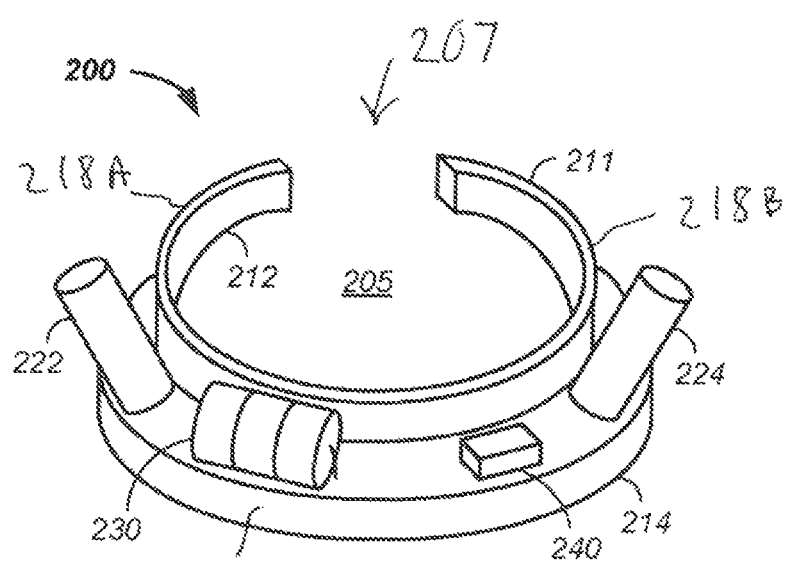
FIG. 2 illustrates an image alignment guide.
Figure 4A:
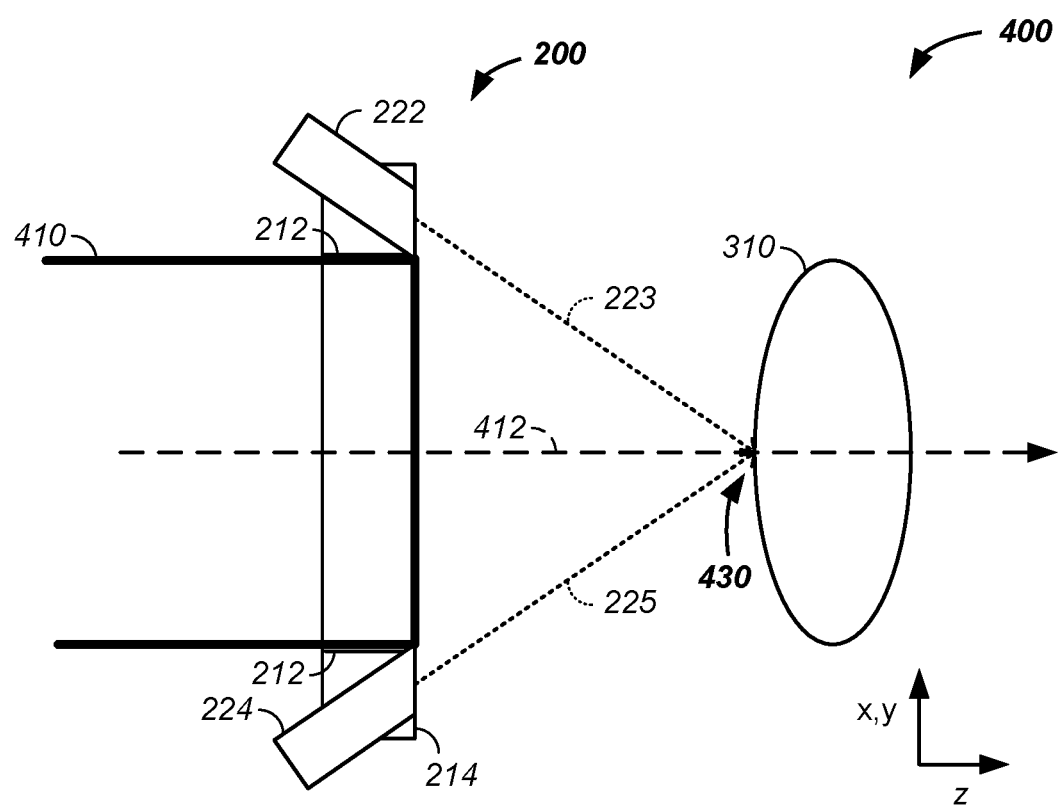
FIG. 4A illustrates the image alignment guide coupled to an imaging system and FIG. 4B illustrates output of the image alignment guide.

Referring now to FIG. 2 and FIG. 4A, an example of the alignment guide 200 is illustrated. Generally, the alignment guide 200 contains an aperture 205, partial aperture, or opening at least partially circumferentially enclosed by a guide wall 211. The guide wall 211 includes arms 218A and B, which extend from base 216. The guide wall 211 optionally and preferably contains an inner perimeter 212, such as an inside diameter, that interfaces with an outer perimeter of a nozzle 410) or output section of the imaging system 400. For example, an inside surface 212 of the guide wall 211 about the aperture 205 of the alignment guide 200 slides over and/or attaches to a nozzle 410 of the imaging system 400, where an imaging beam 412 traverses longitudinally through the nozzle 410 along the z-axis toward a sample 310. In one case, an X-ray imaging system includes an output tube or nozzle through which the imaging beam passes. Output of the alignment guide 200 combined with knowledge of how the alignment guide 200 interfaces to the nozzle 410 and imaging beam 412 of the imaging system 400 is used to aid in relative x-, y-, and/or z-axis placement of the sample 310 in front the nozzle 410 of the imaging system 400, as further described herein.

Referring still to FIG. 2 and FIG. 4A, the alignment guide 200 includes a set of laser elements used to align the imaging system 400 to the sample 310. As illustrated, a first laser 222 and a second laser 224 are mounted, affixed to, and/or embedded into the alignment guide, where output of the first laser 222 and the second laser 224 generate an alignment image, such as an X-image used to align the sample 310 to the imaging system 400. Any number of laser elements are optionally used, such as 2, 3, 4, or more laser elements. For clarity of presentation and without loss of generality, the laser elements are illustrated as connected to the alignment guide 200 and terminating at a front face 214 of the alignment guide 200. Generally, the laser elements, such as the first laser 222 and the second laser 224, are connected to the alignment guide with a known geometry relative to the inner perimeter 212 of the guide wall, which has a fixed x/y-plane position relative to the nozzle 412 and imaging beam 412 of the imaging system 400. Optionally, the alignment guide 200 has a fixed z-axis position relative to the nozzle 410, such as a fixed or mechanically stopped position and/or alignment of the front face 214 of the alignment guide 200 with an exit surface of the nozzle 410.

Still referring to FIG. 2, a power supply 230 and an optional power switch 240 switch are illustrated. Generally, the laser elements use any power supply electrically connected to the laser elements. In this example, a battery and an on/off button respectively represent the power supply 230 and power switch 240. The electromechanical elements of the alignment guide 200 are optionally and preferably enclosed by a guide cover, not illustrated for clarity of presentation.

Figure 3A:
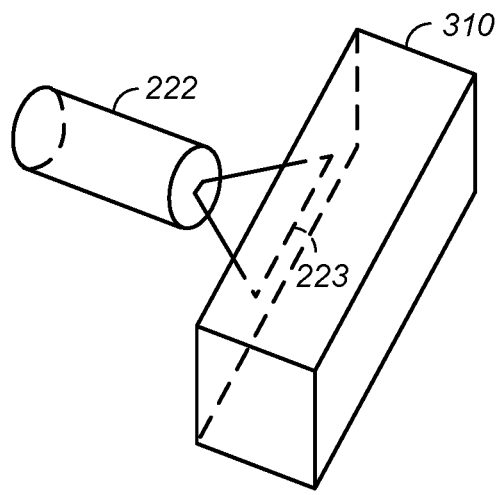
FIG. 3A illustrates a line output of a point laser and FIG. 3B illustrates an 'X' output of the image alignment guide on a sample.

Referring now to FIG. 3A, the first laser 222 is illustrated with a planar output, such as generated using a cylindrical lens, forming a first alignment line 223 on an illuminated object, such as the sample 310. Herein, a cylindrical lens is a lens that forms a line of light on an intersecting surface as opposed to a traditional point on the intersecting surface. For example, the curved face or faces of a cylindrical lens are sections of a cylinder.

Figure 3B:
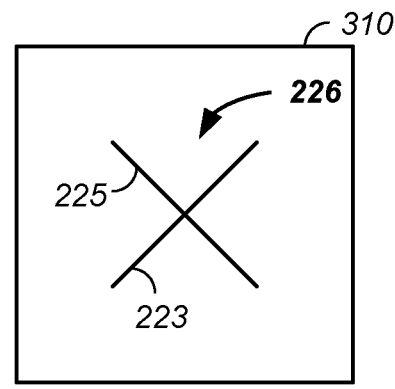

Referring now to FIG. 3B, a targeting image 226 on the sample 310 is formed using output of the set of lasers. In this example, the first laser 222 and the second laser 224 combine to generate an 'X' targeting image, where a first line of the X-image is the first alignment line 223 of the first laser 222 and a second line of the X-image is a second alignment line 225 of the second laser 224. Generally, a target image of any shape is generated, such as any geometric pattern aiding in aligning the imaging beam 412 to an imaging point 430 of the sample 310.

Referring again to FIG. 4A, an example of an interface of the alignment guide 200 to the imaging system 400 is further described. As illustrated, the alignment guide 200 has a known geometric relationship between each of the first alignment laser 222 and second alignment laser 224 to the inner perimeter 212 of the guide wall 211 of the alignment guide 200. Further, the inner perimeter 212 of the guide wall 211 has a known geometric relationship to the nozzle 412 and the imaging beam 412 of the imaging system 400. More particularly, as illustrated the alignment guide 200 is centered on both the nozzle 410 and on the z-axis of the imaging beam 412. Thus, the first alignment line 223 and the second alignment line 225 form the X-image when projected onto the sample 310, where the cross-over point of the X-image is on and/or represents the central z-axis of the imaging beam 412. Thus, by aligning the visible X-image on a desired imaging point 430 of the sample 310, the non-visible imaging beam 412 is centered on the imaging point 430 of the sample. Formation of the X-image is further described herein.

Figure 4B:
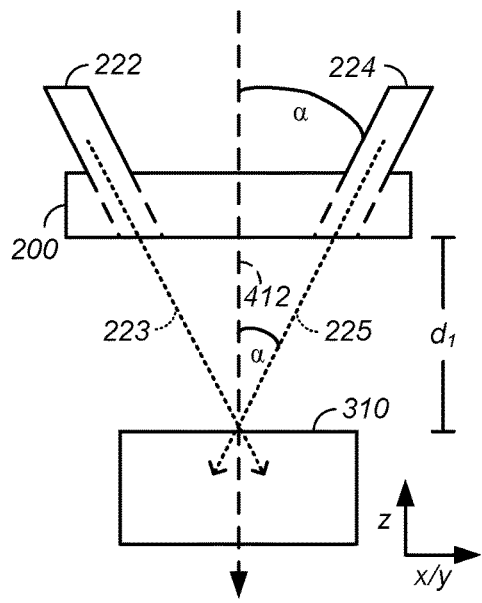

Referring now to FIG. 4B, the alignment guide 200 is illustrated with the second laser 224 orientated at angle alpha, α, relative to a line perpendicular to the aperture 205 and centered in the aperture 205, where the line is the z-axis of the imaging system 400 and imaging beam 412 when the alignment guide 200 is installed on the nozzle 410. Similarly, the first laser 222 is orientated at an angle, such as alpha, relative to the line perpendicular to and centered on the aperture 205. The angle alpha is optionally 1 to 89 degrees, is preferably about 10, 20, 30, 40, or 50 degrees, and is still more preferably about 22, 24, 26, or 28 degrees plus or minus 1 degree. The angles of the set of alignment lasers are optionally used to set the sample at a known distance, d1, from the exit point of the nozzle 410. Optionally and preferably, a first plane of the output side of the exit nozzle is common with a front surface of the alignment guide after installation or at a fixed offset from the first plane to facilitate use of the known distance.

Figure 5A:
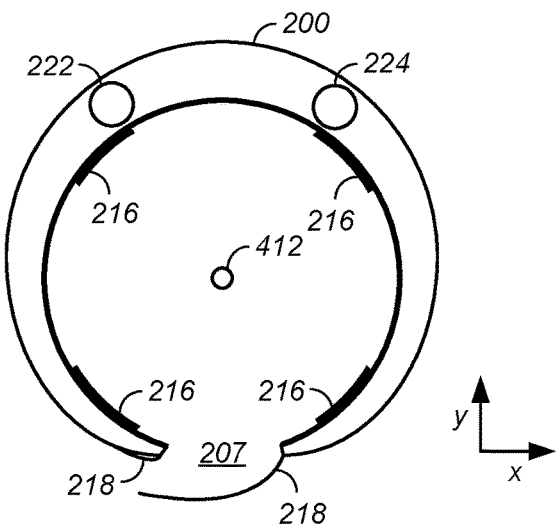
FIG. 5A illustrates an end view of the image alignment guide.

Referring now to FIG. 5A, an example of the alignment guide 200 is provided with an attachment mechanism 218. The attachment mechanism 218 is illustrated as hook and loop fabric connector completing a perimeter of the attachment guide 200 about the aperture 205, with a mating section of the hoop and loop fabric connector present on an opposite side of gap 207. Referring now to FIG. 5C, the attachment mechanism 218 is illustrated as an insert element 219 and a receiving element 217 attached to opposite sides of the gap 207. Optionally, the alignment guide 200 comprises a spring-like flexible material having a lower potential energy in a position self-clamping onto the nozzle 410 compared to a higher potential energy configuration of a temporary flexed open position of the alignment guide 200 when installing the alignment guide 200 to the nozzle 410. Optionally, the attachment mechanism 218 is any mechanism that attaches the alignment guide 200 to the nozzle 410 with a known geometry. Optionally, the attachment mechanism 218 permanently affixes the attachment guide 200 to the imaging system 400. Optionally and preferably, the attachment mechanism 218 facilitates a temporary placement of the attachment guide 200 on a portion of the imaging system 400, such as the nozzle 410, and removal of the attachment guide 200 from the imaging system 400, such as for placement on a second imaging system.

Referring again to FIG. 5A, the alignment guide 200 is illustrated with optional gripping elements 216 that reduce/ prevent sliding of the alignment guide 200 along a z-axis of the nozzle 410. For example, the gripping elements comprise a friction tape and/or a thin tape or section of rubber. The optional gripping elements 216 still yield a known relationship of the set of lasers to the imaging beam 412.

Figure 5B:
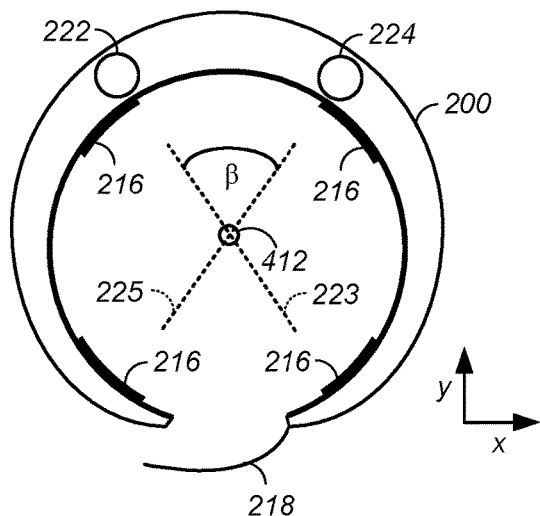
FIG. 5B illustrates a first 'X' output of the image alignment system relative to an imaging beam.
Figure 5C:
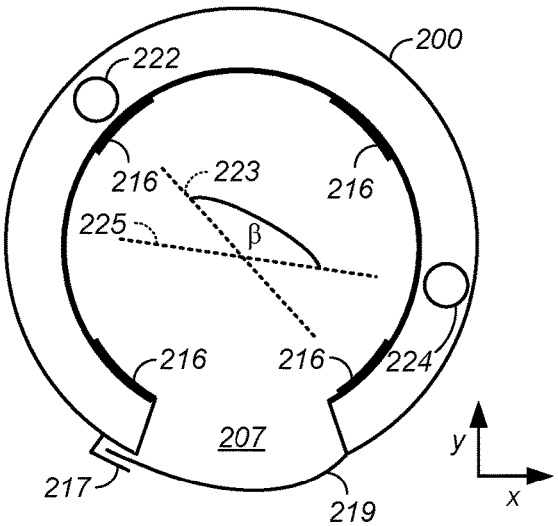
FIG. 5C illustrates a wide angle 'X' output of the image alignment guide.

Referring now to FIG. 5B, the first laser 222 and output thereof forms the first alignment line 223 on a surface of the sample 310 and the second laser 224 and output thereof forms the second alignment line 225 on the surface of the sample 310, where the formed X-image has an angle beta, β, between the lines of the X-image. The angle beta is a result of the relative positions of the first laser 222 and the second laser 224 on the alignment guide 200. For example, referring now to FIG. 5C, a larger angle beta is formed using a larger angle between the first laser 222, a center of the aperture 205, and the second laser 224. However, the X-image is still formed with beta angles from 1 to 179 degrees, with a preferred beta angle within 10 degrees of 20, 40, 60, 80, 100, 120, 140, and 160 degrees.

Referring again to FIG. 2, FIG. 5B, and FIG. 5C, the alignment guide 200 is respectively illustrated with three separate geometries. The inventor notes that the alignment guide 200 is optionally of any geometry forming a known geometry of a visible alignment signal on the sample where the alignment signal indicates a location of the imaging beam, which is not visible and/or is invisible to the human eye.

Several examples illustrate use of the alignment guide 200.

Example I

In a first example, the alignment guide 200 is manufactured with an aperture of about 1 to 5 inches. The inventor notes that only a few standard nozzle diameters are used in X-ray systems and thus the aperture is optionally designed to the known and commercially distributed nozzles. For instance, a first standard diameter of an X-ray nozzle is 2¾ inches. Thus, an alignment guide with a 2¾ inch nominal inside diameter that flexes open to about 3 inches during installation is a logical design. Optionally, the attachment mechanism 218 allows a standard aperture to be cinched down onto smaller nozzles, such as to a 1, 2, or 2½ inch nozzle diameter.

Example II

In a second example, the alignment guide 200 attaches to an X-ray nozzle of a portable X-ray system. For instance, the X-ray nozzle is integrated to the X-ray system in a manner that allows the X-ray nozzle, as a carryable unit, to be orientated proximate a desired imaging site.

Example III

In a third example, the alignment guide 200 is attached to an exit nozzle of the imaging system and the imaging system is used to image a pet at a specified position, such as a femur when diagnosing a potentially broken bone.

Still yet another embodiment includes any combination and/or permutation of any of the elements described herein.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method for aligning an imaging beam, longitudinally passing through an exit nozzle of an existing imaging system, to an imaging area of a sample, by way of a retrofittable alignment guide, comprising the steps of:

providing an alignment guide, said alignment guide comprising
a base,
a guide wall partially circumferentially enclosing a central aperture, said guide wall having an inner guide wall surface, the guide wall including curvilinear first and second arms attached to the base and curvingly extending towards each other and terminating to define a gap, a first laser element connected to said base at a first angle, said first laser element configured to project a first alignment visible image onto the sample during use; and a second laser element connected to said base at a second angle, said second laser element configured to project a second alignment visible image onto the sample during use:

orienting said inner guide wall surface, of said guide wall, of said alignment guide, to proximately contact the exit nozzle of the imaging system by flexing the first and second arms to permit attachment to the exit nozzle of the imaging system;

projecting an output beam of the first laser element of the alignment guide onto the sample to form the first alignment visible image;

projecting an output beam of the second laser element of the alignment guide onto the sample to form the second alignment visible image; and aligning the imaging beam of the imaging system to the imaging area of the sample using said first alignment visible image and said second alignment visible image.

2. The method of claim 1, said step of aligning further comprising the step of:

relatively positioning the sample and the exit nozzle of the imaging system to intersect an alignment point with the imaging area of the sample, said first alignment visible image comprising a first alignment line, said second alignment visible image comprising a second alignment line crossing the first alignment line at the alignment point.

3. An apparatus for aligning an imaging beam, longitudinally passing through an exit nozzle of an imaging system, to a sample, the apparatus being attachable to and detachable from the exit nozzle of the imaging system comprising:

an alignment guide base;

a curvilinear guide wall partially circumferentially enclosing a central aperture through which the exit nozzle of the imaging system extends when the apparatus is attached thereto during use said guide wall having an inner surface configured to contact an outer surface of the exit nozzle during use, the guide wall including curvilinear first and second arms attached to the alignment guide base and curvingly extending towards each other and terminating to define a gap which facilitates flexing of the first and second arms to permit attachment and detachment of the apparatus from the exit nozzle;

a first laser element connected to said alignment guide base at a first angle, said first laser element configured to project a first alignment visible image onto the sample during use;

a second laser element connected to said alignment guide base at a second angle, said second laser element configured to project a second alignment visible image onto the sample during use, and said first alignment visible image and said second alignment visible image combining to represent a relative position of the imaging beam on the sample.

4. The apparatus of claim 3, said alignment guide base further has a flat front face, wherein a first axial alignment line perpendicular to said front face and a first longitudinal axis of said first laser element intersect at the first angle ($\alpha$), and wherein the first axial alignment line and a second longitudinal axis of said second laser element intersect at the second angle.

5. The apparatus of claim 4, said first angle is between thirty degrees and forty-five degrees.

6. The apparatus of claim 5, said first laser element forms the first alignment visible image in the form of a first projected alignment line on the sample during use, said second laser element forming the second alignment visible image in the form of a second projected alignment line on the sample during use, the first projected alignment line and the second projected alignment line intersecting at a point on the sample indicating a centered position of the imaging beam on the sample.

7. The apparatus of claim 6, further comprising:

means for fixedly replaceably attaching said alignment guide to the exit nozzle of the imaging system, said means for fixedly replaceably attaching comprising at least one of:

a hook and loop fabric connector.

8. The apparatus of claim 6, further comprising:

an on/off selector element electrically linked to a power supply and said first laser element.

9. The apparatus of claim 6, the aperture having a diameter between one-half inch and four inches.

10. The apparatus of claim 3, wherein a first guide line passing longitudinally through said first laser element and an imaging line passing longitudinally through the exit nozzle form the first angle at the sample area during use.

11. The apparatus of claim 10, wherein a second guide line passing longitudinally through said second laser element and the imaging line form the second angle at the sample area during use.

12. The apparatus of claim 3, wherein said first laser element, a center of the aperture, and the second laser element form an angle between ten degrees and one hundred seventy degrees.

13. A method for aligning an imaging beam, longitudinally passing through an exit nozzle of an imaging system, to an imaging area of a sample, comprising the steps of:

providing an alignment guide, said alignment guide comprising:

a base, a guide wall partially circumferentially enclosing a central aperture, the guide wall including first and second curvilinear arms attached to the base and curvingly extending towards each other and terminating to define a gap;

a first laser element connected to said base; and a second laser element connected to said base;

inserting the exit nozzle of the imaging system into the aperture of the alignment guide;

projecting a first line from said first laser element of the alignment guide onto the sample;

projecting a second line from said second laser element of the alignment guide onto the sample;

moving the sample relative to the exit nozzle to position an intersection of the first line and the second line at the imaging area to align the imaging beam to the imaging area.

\* \* \* \* \*